(12) United States Patent
Wolfenson Band et al.

(10) Patent No.: US 7,022,822 B1
(45) Date of Patent: Apr. 4, 2006

(54) HIGHLY PURIFIED GONADOTROPIN COMPOSITIONS AND PROCESS FOR PREPARING THEM

(75) Inventors: Claudio Fernando Wolfenson Band, Buenos Aires (AR); Liliana Ester Balanian, Buenos Aires (AR); Jose-Felipe Groisman, Buenos Aires (AR); Erundina Marta Fasanella, Olivos Buenos Aires (AR)

(73) Assignee: Instituto Massone S.A., Buenos Aires (AR)

( * ) Notice: Subject to any disclaimer, the term of this patent is extended or adjusted under 35 U.S.C. 154(b) by 0 days.

(21) Appl. No.: 09/958,802

(22) PCT Filed: Apr. 14, 2000

(86) PCT No.: PCT/EP00/03357

§ 371 (c)(1),
(2), (4) Date: Jan. 15, 2002

(87) PCT Pub. No.: WO00/63248

PCT Pub. Date: Oct. 26, 2000

Related U.S. Application Data

(60) Provisional application No. 60/129,540, filed on Apr. 16, 1999.

(51) Int. Cl.
*C07K 1/00* (2006.01)
*A23J 1/00* (2006.01)
*A61K 38/16* (2006.01)

(52) U.S. Cl. ...................... 530/398; 530/397; 530/412; 530/416; 530/417; 530/418; 530/419; 530/427; 514/8; 514/12

(58) Field of Classification Search ................ 530/398, 530/397, 412, 416, 417, 418, 419, 427; 514/8, 514/12
See application file for complete search history.

(56) References Cited

FOREIGN PATENT DOCUMENTS

GB     1 065 127 A   *   4/1967
WO    WO 98 20039 A  *   5/1998

OTHER PUBLICATIONS

Birken et al., Methods: A Companion to Methods in Enzymology, vol. 21, No. 1, pp. 3-14, 2000.*

* cited by examiner

*Primary Examiner*—Jon Weber
*Assistant Examiner*—Abdel A. Mohamed
(74) *Attorney, Agent, or Firm*—Crowell & Moring LLP

(57) ABSTRACT

Purification process of humanPurification process of human urinary gonadotropins of high biological activity and chemical purity absolutely free of foreign contaminating materials derived from the use of biological reagents or chromatography dyes, from crude of gonadotropins. The high biological activity and chemically pure composition of human gonadotropins obtained by this process, are used for the treatment of infertility and are selected from the group of follitropin or menotropins, having a bioactivity greater than 2500 IU/mg protein as tested by biological assay in rats, for both FSH and LH hormones for menotropins and greater than 5000 IU/mg protein for follitropin having an FSH:LH ratio about 75:1. Pharmaceutical preparations of said gonadotropins free of these contaminating materials are also comprised within the present invention.

9 Claims, 10 Drawing Sheets

Figure 1: Electrophoresis of the conventional product (HMG) vs. the new highly purified menotropins product (Fraction $K_M$).

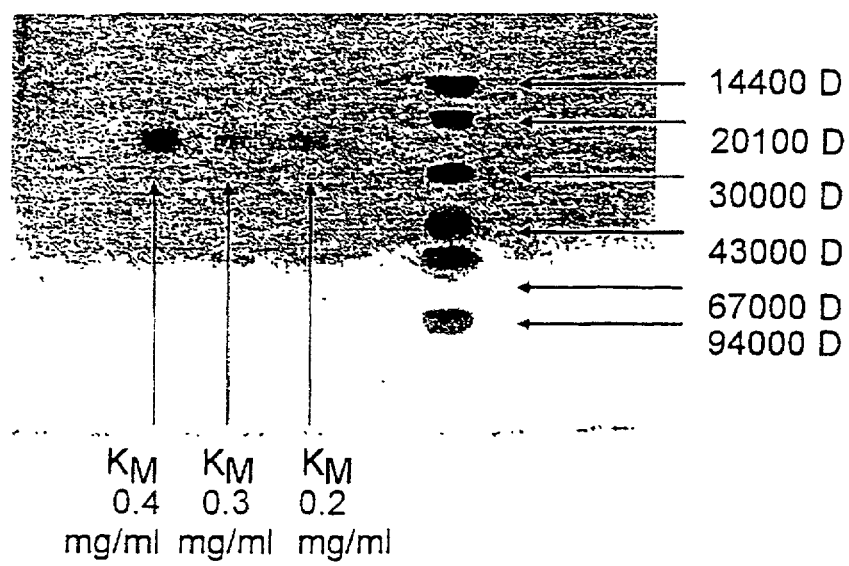
Figure N° 2: Polyacrylamide Gel Electrophoresis of highly purified Menotropins (Fraction $K_M$) run in different concentrations together with the molecular weight standards.

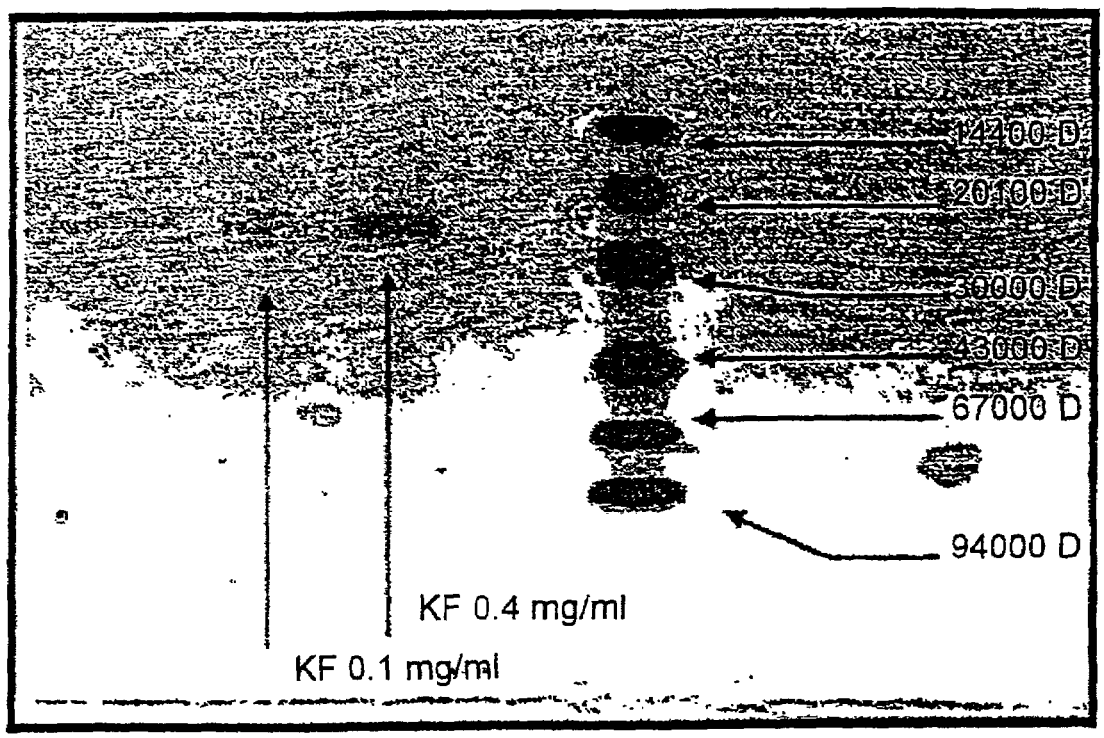
Figure N°3: Polyacrylamide Gel Electrophoresis of a highly purified FSH (Fraction $K_F$) run in different concentrations together with the molecular weight standards.

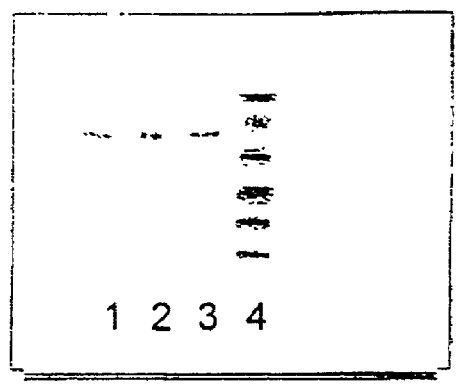
Figure N° 4: Polyacrylamide Gel Electrophoresis (PAGE) of:
 1 - Gonal-F (Serono) 1 FSH IU/µl
 2 - Metrodine HP (Serono) 3 FSH IU/µl
 3 - Highly Purified Menotropins (Fraction $K_M$) 3.7 FSH IU/µl
 4 - Molecular Weight Standards (from the top): 14,400 D, 20,100 D, 30,000 D, 43,000 D, 67,000 D and 94,000 D.

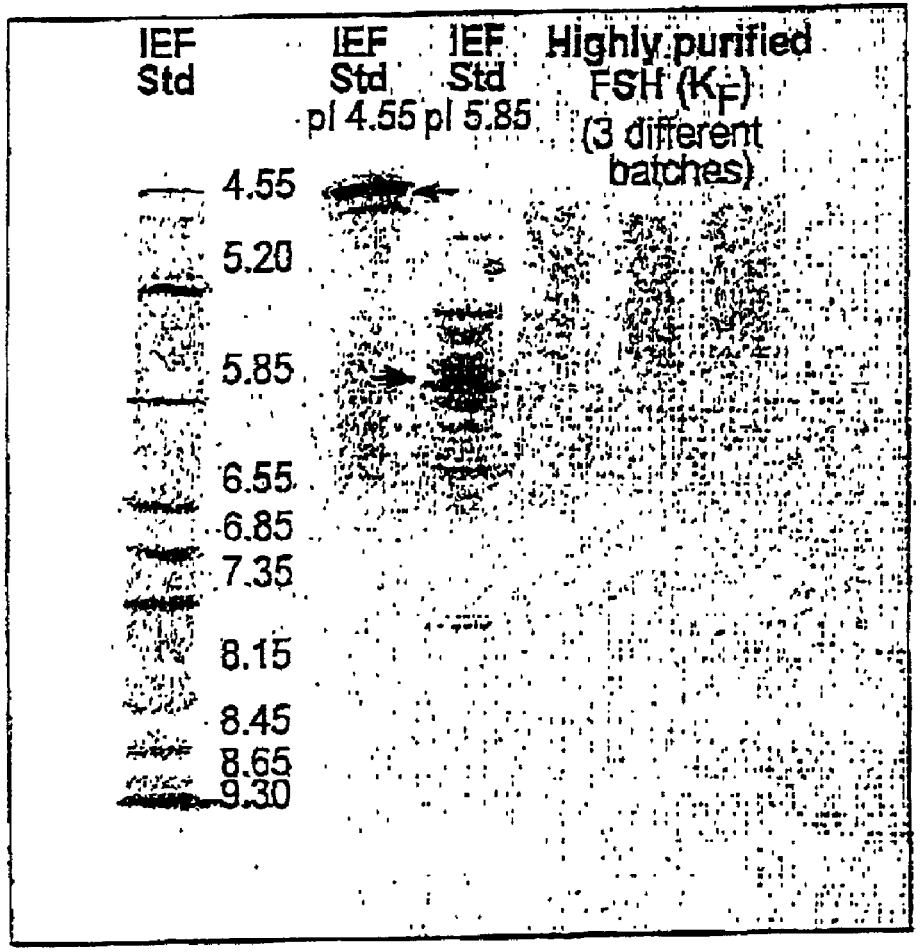
Figure No 5: Isoelectric focusing on 3-10 PhastGels silver stained.
Lane 1: Calibration Kits for Broad 3 - 10 pI.
Lane 2: pI 4.55 standard (soybean trypsin inhibitor).
Lane 3: pI 5.85 standard (bovine carbonic anhydrase B).
Lane 4,5 and 6: highly purified follitropin ($K_F$) product (3 different production batches).

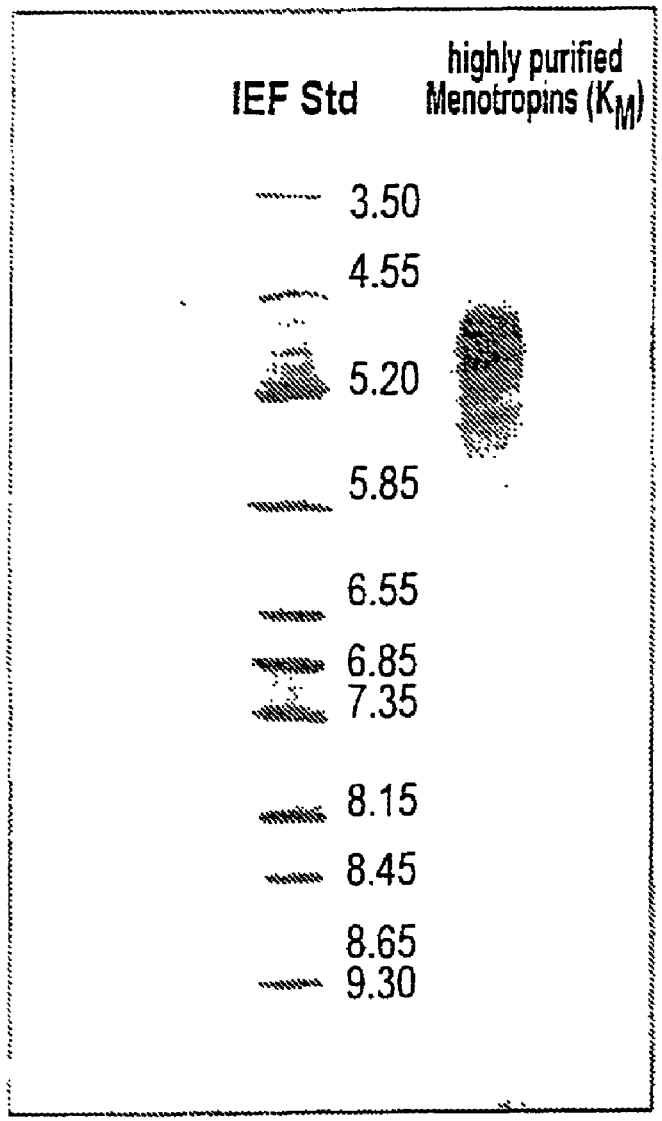
Figure No 6: Isoelectric focusing on 3-10 PhastGels silver stained.
Lane 1: Calibration Kits for Broad 3 - 10 pI.
Lane 2: highly purified menotropins ($K_M$) product.

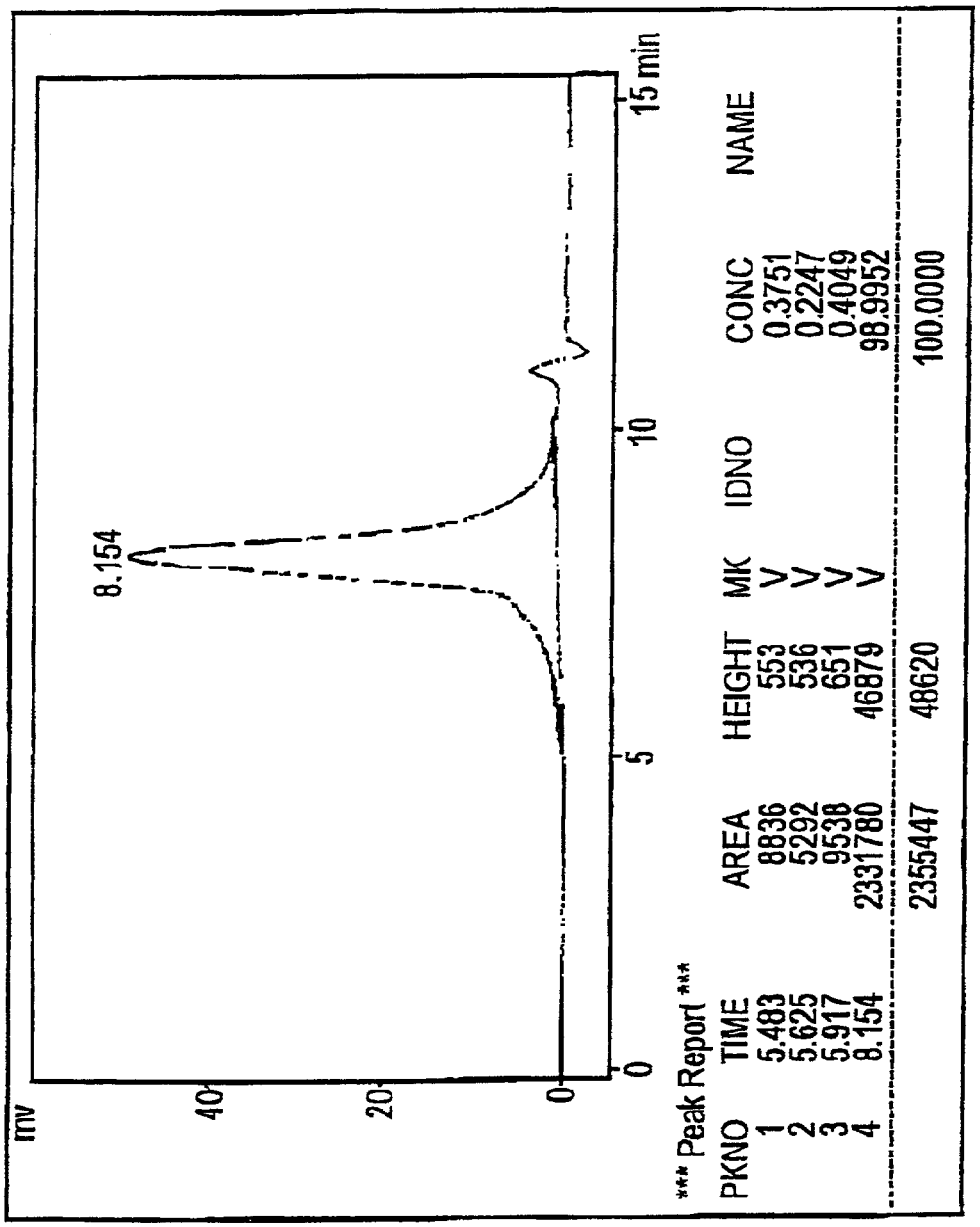
Figure N° 7: Result obtained by HPLC with a Highly Purified Menotropins (Fraction $K_M$) sample.

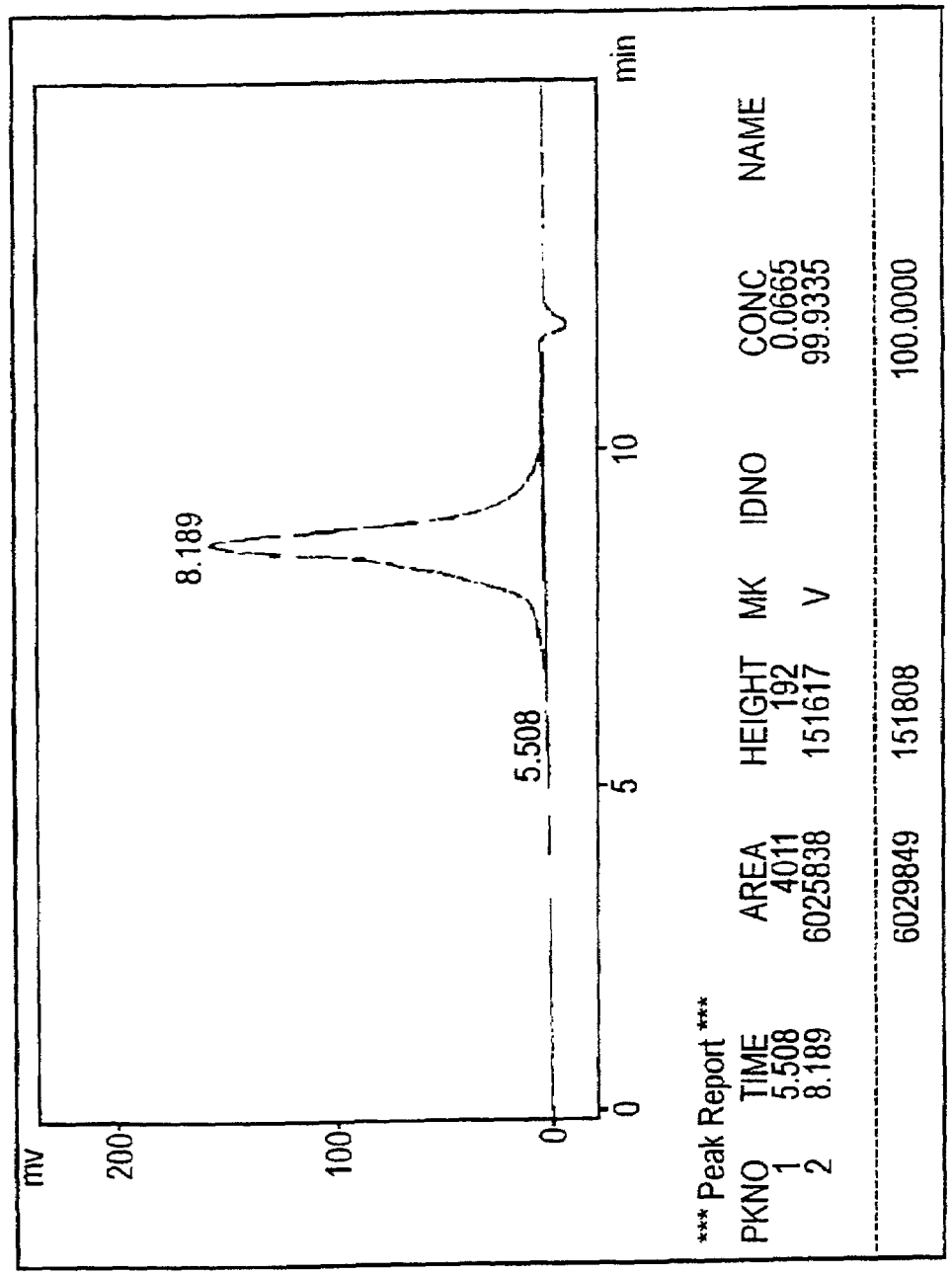
Figure N° 8: Result obtained by HPLC with a Highly Purified FSH (Fraction $K_F$) sample.

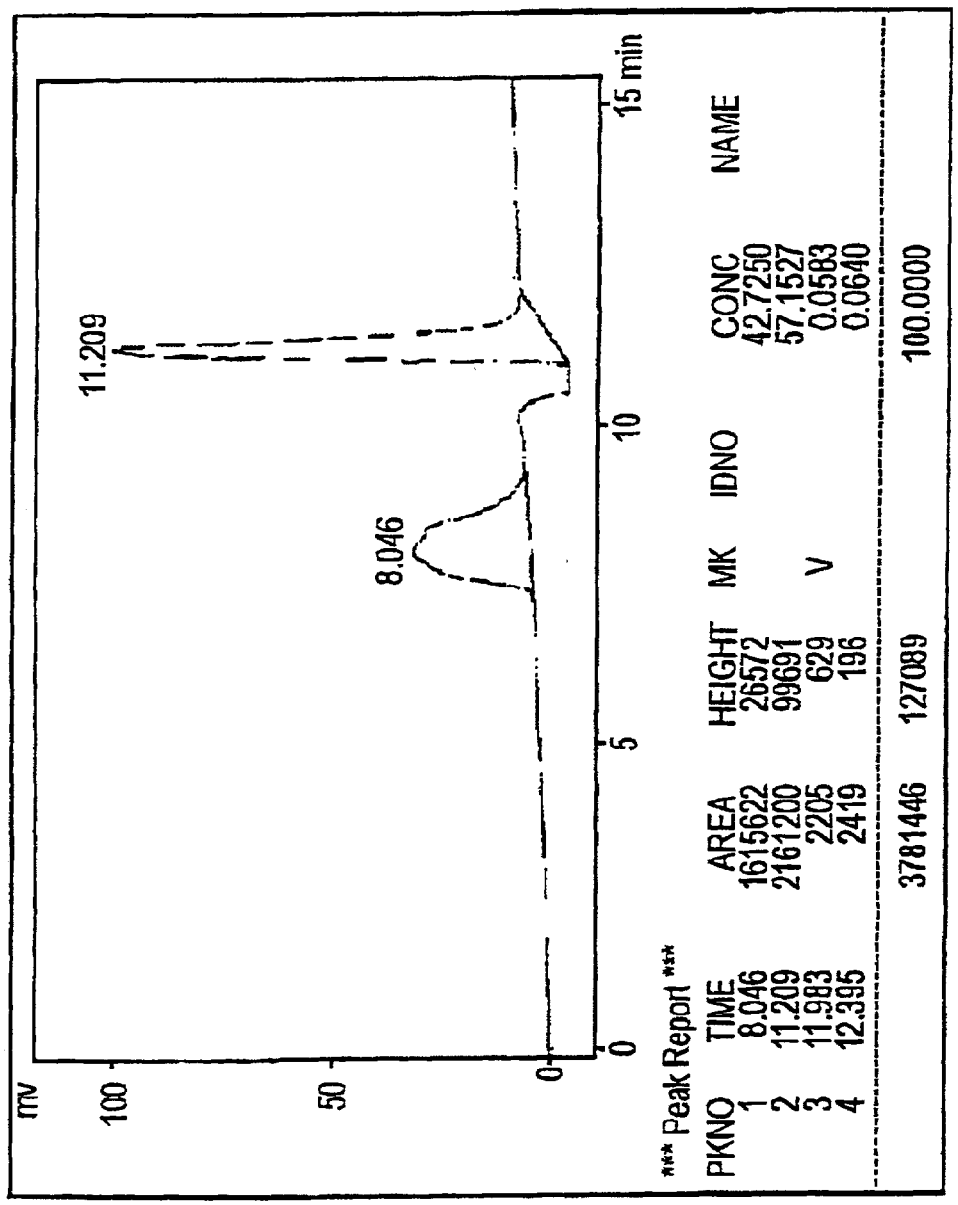
Figure N° 9: Result obtained by HPLC with a sample of Gonal-F (Serono).
Note: The peak at retention time 11.2 corresponds with an excipient of the pharmaceutical preparation.

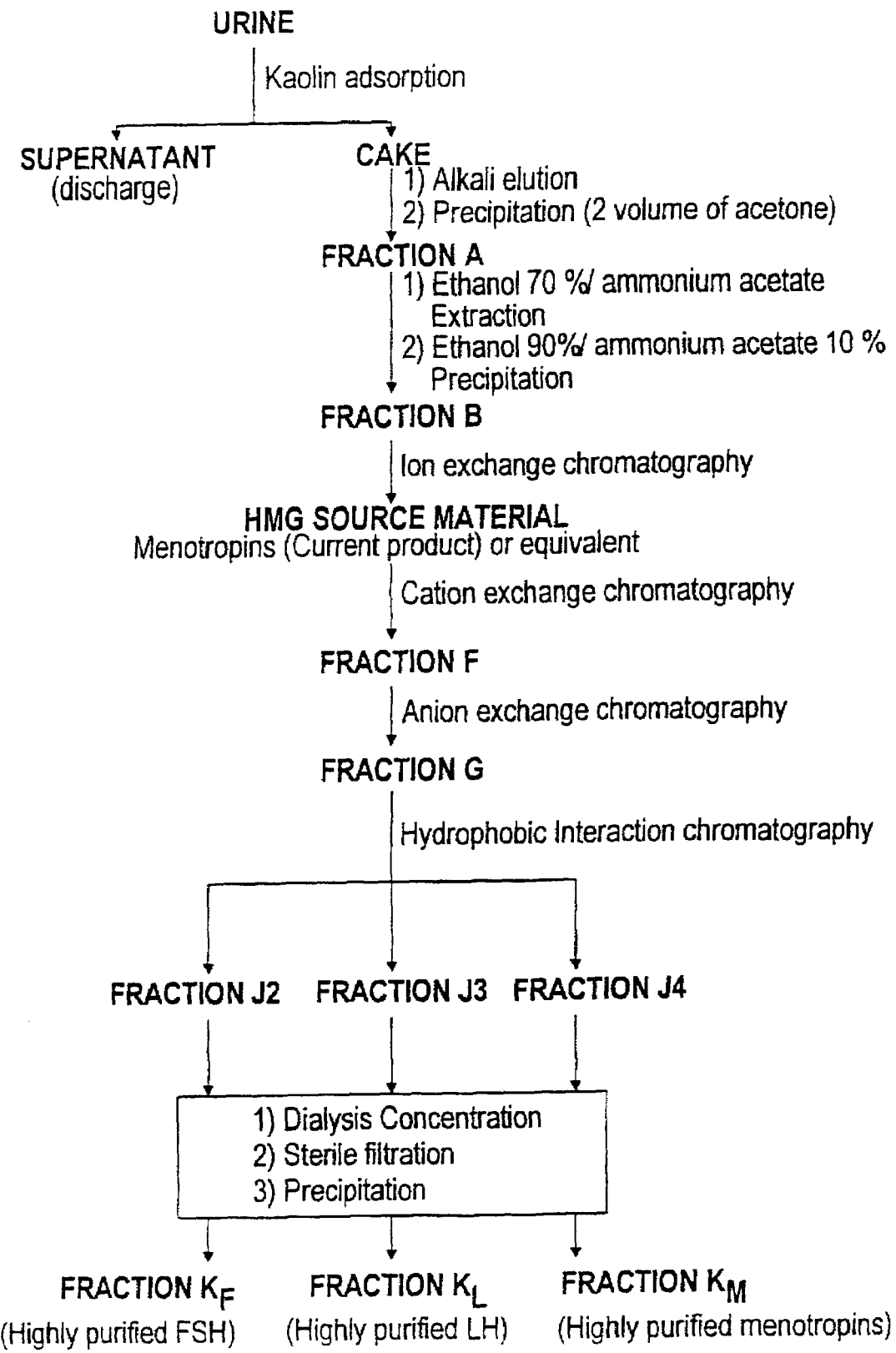
Figure N° 10: Flow chart for obtaining highly purified gonadotropins.

HIGHLY PURIFIED GONADOTROPIN COMPOSITIONS AND PROCESS FOR PREPARING THEM

The present invention relates to gonadotropin compositions, particularly to FSH (follicle stimulating hormone: follitropin) and menotropin compositions of high biological activity and to a method for preparing these compositions from human urine crude of menopausal or postmenopausal women. The chemical purity obtained is greater than 95% as measured by HPLC, whereas the specific biologic activity is greater than 2500 IU/mg protein for both FSH and LH hormones for menotropin composition (Human Menopausal Gonadotropins; HMG) and greater than 5000 IU/mg protein for FSH.

BACKGROUND OF THE INVENTION

The term "menotropins" is applied to a hormonal combination obtained from menopausal and post-menopausal women's urine comprising two glycoprotein hormones: follicle stimulating hormone and luteinizing hormone. These two hormones are secreted by the pituitary gland, and subsequently metabolized and excreted in the urine.

Menotropins and follitropin have been long used in the therapeutical treatment of infertility disorders.

The role of FSH consists in acting on the ovarian follicles, promoting their rapid growth and maturity with subsequent ovulation or atresia. FSH along with LH is also involved in the biosynthesis of estradiol in the ovarian follicles that it has stimulated. The internal theca is the main site of androgen follicular biosynthesis which is under the control of LH. Controlled by FSH, this androgen is then aromatized in the granulose cells and excreted to the blood torrent. Therefore, LH is a necessary constituent along with FSH in follicular stimulation.

Pituitary hormones FSH and LH. thyroid stimulating hormone (TSH) and the placental hormone human chorionic gonadotropin (HCG) are closely related since all of them are glycoproteins having in their structure two subunits called $\alpha$ and $\beta$. Both subunits are bound by non-covalent interaction. These subunits do not have any biological activity separately. The $\alpha$-chains of the four above-mentioned hormones are common, while the $\beta$-chains are different and provide a biological activity characteristic of each hormone. However, important portions of the $\beta$-chain are also common, which can be particularly observed in LH and HCG $\beta$-chains.

Gonadotropins obtained from human urine have been partially purified until reaching biosafety characteristics compatible with the requirements of an injectable pharmaceutical product, and have been commercialized for more than 30 years in order to solve infertility problems; being in the form of an injectable grade pharmaceutical preparation, they are listed in the most important pharmacopoeias in the world and have been approved for pharmaceutical use in practically all countries all over the world.

The composition of the follitropin preparation can be described as follows:
Follicle stimulating hormone: 75 or 150 International units of FSH
Excipient (required for the lyophilization process, generally 5–20 mg of lactose) and other non-active proteins.

The composition of the menotropin preparation can be described as follows:
Follicle stimulating hormone: 75 or 150 International units of FSH
Luteinizing hormone 75 or 150 International units of LH
Excipient (required for the lyophilization process, generally 5–20 mg of lactose) and other non-active proteins.

International units of FSH and LH are calculated by measuring the biological activities in rats relative to an international standard prepared by the National Institute for Biological Standards and Control (NIBSC) dependent on the World Health Organization.

The requirement, imposed by Pharmacopoeias such as United States Pharmacopoeia (USP XXIII) or British Pharmacopoeia (BP) in terms of purity of the starting material required for the preparation of injectable grade menotropins, consists in a starting material having an FSH activity greater than 40 IU/mg and an LH activity greater than 40 IU/mg. In view of this, those starting materials heretofore used have been obtained by a manufacturing process ensuring an activity in the range of 70–150 IU FSH/LH per mg., which is more than enough to meet the requirements imposed by the health organizations as far as biosafety and effectiveness are concerned.

However, the latest developments in terms of purification techniques and the development of gonadotropins from recombinant origin have influenced the need for preparations of highly purified native gonadotropins of urinary origin, without the presence of impurifying proteins.

Some FSH and LH purification process have been described in the recent past.

EP 0 322 438 B1 and the equivalent U.S. Pat. Nos. 5,128,453; 5,767,067 and 5,840,857 refer to the preparation of follicle stimulating hormone with high specific activity from urinary origin. However these processes include a specific monoclonal antibodies step. From the safety point of view, this fact raises some concerns about contamination of the product with heterologous proteins, DNA residues from the hosts cell and viruses. Although process validations and final testing can help to exclude the possibility of potential contamination, it is reasonable to judge that a process that is specially designed to avoid using biological reagents has higher safety standards than the one which includes this type of purification step.

The WO 98/20039 patent application describes a FSH and LH separation and purification process which avoids employing biological reagents. However, due to the very high FSH:LH ratio of the raw material used and products obtained, this process excludes the possibility of obtaining menotropins, a preparation which requires an FSH:LH ratio of approximately 1:1

Moreover, WO 98/20039 fails to characterize the gonadotropins obtained as a bioactive material, which is an essential issue for a therapeutical product. This patent application uses an immunoradiometric method to test the activity, a determination method that arises deep concerns about its accuracy.

In fact, it has been long recognized that the structural heterogeneity of FSH and LH isoforms has an important impact on the biological activity and immunological reactivity of both hormones [Costagliola et. al. J. Endocrinol. Invest. 17, 291 (1994)]. Observed differences in bio- and immuno-FSH and LH levels suggest that separated structural entities are recognized by the bioassays versus the immunoassay. It has been thoroughly discussed that immunoassays does not consistently provide a good estimation of the bioactive gonadotropins level and does not necessarily reflect the biological activity [Dahl and Stone, J. Andrology, 13, 11 (1992); Rose et. al Endocrine reviews 21, 5 (2000)].

On the other hand, bioassays are considered to be the proper test to define the hormone activity since it takes into account two important components that are absent in others methods: the biological action at the target tissue and the biological clearance [Rose et. al. Endocrine reviews 21, 5 (2000)]. This fact makes the in vivo bioassay mandatory for calibration of therapeutics preparations [Rose, Clinica Chimica Acta 273, 103 (1998)].

It must be also underlined that the WO 98/20039 fails also to characterize the gonadotropins as a chemically pure drug since no analytical method is presented to support this fact.

The present invention presents a full characterization of the gonadotropins not only from the bioactivity scope but also from the analytical point of view by introducing sensitive analytical method to test the purity. Since the assays used to establish the FSH and LH activity in the present invention are, in all the cases, in vivo bioassays which has been long proved to be a robust specific test for assuring bioactivity, the potency of the FSH and the LH for each gonadotropins obtained and also their ratio can be assured.

A second issue to consider is that the above mentioned patent (WO 98/20039) describes the use of an affinity dye chromatography to purify gonadotropins. This procedure could arise some concern about the potential contamination of the product by the leakage of the dye. These kind of foreign compounds are not desirable in products to be injected into humans [Protein Purification by R. K. Scopes, Springler-Verlag New York Inc; 2nd Edition, page 156 (1998)]. Since the present invention was design to exclude this type of chromatography, the dye contamination problem is an issue completely avoided.

Current menotropins (the commercially available product) may suffer the drawback of potential local allergic reactions when they are administered subcutaneously, due to the presence of protein contaminants.

This invention provides a method for the purification and the preparation of the first commercially available high purity gonadotropin products. This methodology was specially designed so as to avoid using biological reagents such as antibodies, receptros and other heterologus materials and chromatography dyes. Besides the safety issue, the use of non-specific steps during the isolation allows to obtain of all the isoforms that are present in the starting material.

As extensively described, heterogeneity is of particular importance in the glycoprotein hormones. At least 20–30 different isoforms of FSH, LH and TSH exist (Wide, Acta Endocr., Copenh 109, 181–189, 1985). These isoforms differ in their molecular weight and charge. Although glycoprotein hormone isoforms mainly vary in the oligosaccharide structure, microheterogeneities may be also present from differences in the amino-acid composition (Costagliola et al, J. Endocrinol. Invest., 17, 291–299, 1994; Wilson et al., J. Endocrinol 125, 3–14, 1990).

It is generally accepted that the type of different isoforms isolated depends, among other factors, on the isolation techniques (Cockburn et al., Biologicals 19, 257–264, 1991). The use of highly discriminating techniques for isolation, such as monoclonal antibodies, can contribute to select only one part of the isoforms present in the source of the material. Being "too specific", some biologically active gonadotropin variants may not be recognized by the antibodies and could be lost (Costagliola et al, J. Endocrinol. Invest., 17, 291–299, 1994). On the other hand, a non-selective approach, such as the one described in this patent, can be useful in purifying all the types of isoforms present in the urine. Different isoforms have shown to vary with respect to the interaction with the cell surface receptors and metabolic clearance (Thotakura et al., Glycobiology 5, 3–10, 1995). Oligosaccharide structure is under the control of various physiological factors. From the therapeutical point of view, it is interesting to have a product in which all isoforms present in the urine are available. In this way, the highly purified products described here provide the differential roles of naturally occurring gonadotropin isoforms in the maintenance of reproductive function.

It must also be underlined that the present application is the first characterization of a highly purified menotropins preparation that was confirmed not only by its high biological potency but also by relevant screening methods (PAGE electrophoresis, HPLC, size exclusion chromatography).

Being now available in a purified grade and in a large scale, these naturally occurring FSH and LH molecules can be then investigated and carefully analyzed. The three dimensional structure of the hormones can contribute to a better understanding about the role of the oligosaccharides.

The method for obtaining currently produced menotropins is well known. As indicated in BP 1980, menotropins can be prepared from post-menopausal women's urine by kaolin adsorption, subsequent alkali elution and precipitation with 2 volumes of acetone. The required fraction is extracted from this precipitate with an ammonium acetate solution in 70% ethanol and then precipitated with a 10% ammonium acetate solution in 90% ethanol. The menotropins product is obtained by ionic exchange chromatography of this precipitate.

The starting material, from now on the "HMG source material", that can be used in the present invention for obtaining highly purified menotropins, constitutes the menotropins specialty, as specified in the pharmacopoeias (USP XXIII, BP 1993 addendum 1995; EP 1986) or any other material closely related to this specialty. Therefore it is understood that this preparation process is also applicable to other materials that do not strictly meet the requirements applicable to menotropins. In fact, satisfactory results were obtained using Fraction C (see description of the invention. Example 1 and example 2), which is a material that falls to comply with the FSH:LH ratio menotropins requirement (FSH:LH, 1:1, approximately) Moreover, the present invention provides a procedure to adjust the FSH:LH ratio when needed being therefore capable of providing highly purified menotropins specialty even when starting materials which are out of the correct FSH:LH ratio are used. Thanks to this, it is possible to obtain a product comprised of FSH and LH in the appropriate ratio 1:1 necessary to produce the pharmaceutical preparation, without having separated both active principles during purification. That is to say, accomplishing the co-purification of both hormones, from a purity degree of approximately 5% in the starting material to more than 95% in the final product with a final potency 25–35 times greater than the initial one. The purification degree as obtained can be visualized from FIG. 1, which shows the result of polyacrylamide gel electrophoresis of the conventional pharmaceutical product vs. the new purified version obtained from the application of the present Invention.

The steps described in the present invention can be used following in a different order from the one herein described, which does not imply varying the invention philosophy. Equally satisfactory results were obtained by inserting, for example, the hydrophobic interaction resin between the two ionic exchange chromatography steps described later.

This invention also provides for the preparation of urinary gonadotropins separately, that is to say FSH and LH.

The administration of menotropins compositions for therapeutic purposes has been carried out, mainly by intramuscular injection. This administration form creates a considerable discomfort in the patient and requires from the patient regular visits to clinical units, sometimes for weeks or months in order to receive the treatment.

Subcutaneous administration would make the self-administration possible and consequently improve patient's cooperation and compliance.

The subcutaneous administration of urinary gonadotropins has already been described (Nakamura Y., et al, Fertil Steril 51, 423–429, 1989; Engmann L. et al. Fertil Steril. 69, 836–840, 1998). The subcutaneous administration of non-pure preparations may suffer the drawback of local allergies due to the presence of impurities in the product used and consequently result in the suspension of the treatment. Therefore it is worthwhile to produce high purity products which can diminish the possibility of these allergic reactions.

SUMMARY OF THE INVENTION

The present invention relates to FSH and/or LH compositions of high biological activity and a method for preparing these compositions from human urine crude of menopausal or postmenopausal women. The chemical purity is greater than 95% as measured by HPLC, whereas the specific biologic activity is greater than 2500 IU/mg protein for the FSH and LH for menotropins and greater than 5000 IU/mg for follitropin.

The compositions of the invention may comprise: any conventional excipient such as hexoses, mannitol and mixtures thereof, a stabilizer selected from the group of albumin, detergents and mixtures thereof.

The injectable compositions obtained are substantially free of contaminants and can be adapted for subcutaneous administration.

The follitropin and/or menotropins compositions of the present invention may be used to prepare a pharmaceutical preparation of high biological activity and chemical purity that comprises or not a pharmaceutically acceptable carrier.

The separation and purification process of human urinary gonadotropins of high biological activity and chemical purity from crude of gonadotropins, including HMG source material, absolutely free of foreign contaminating materials derivated from the use of biological reagents or chromatography dyes comprising mainly the following steps, in any order:

1) purification of said gonadotropins crude diluted in 0.05–0.15 M ammonium acetate, pH 5.0–6.0, in an ionic exchange column with a strong cationic resin of the type of sulphopropyl, eluting both FSH and LH with solutions of 0.05–0.5 M ammonium acetate, pH 5.0–7.0; and
2) purification of this fraction diluted in 0.01–0.05 M ammonium acetate, pH 5.0–7.0 in a column of ionic exchange with a strong anionic resin of the ammonium quaternarium type, eluting both FSH and LH with solutions of 0.05–0.2 M ammonium acetate, pH 5.0–7.0; and
3) purification of gonadotropins in a column with an hydrophobic interaction resin by the sequencial addition of at least two of the following solutions:
a) buffer of 50–200 mM sodium phosphate, and 0.8–1.2 M ammonium sulfate, pH 5.0–6.0;
b) buffer of 50–200 mM sodium phosphate, and 0.4–0.6 M ammonium sulfate; pH 5.0–7.0;
c) buffer of 50–200 mM sodium phosphate (50–70% v/v), and ethanol 96% (50–30% v/v).

wherein said steps may be performed in any order.

Resins of the type of SP-Sepharose, Q-Sepharose and hydrophobic interaction resins may be used in these steps. A preferred hydrophobic interaction resin is a Phenyl-Sepharose resin.

The process of the invention further comprises secondary steps of precipitation, centrifugation, ultrafiltration, dialysis, washing, drying in vacuo, and cooling. The last step of this process may be selectively performed to obtain fractions that have only menotropins, FSH or LH activities.

One of the main advantages of the process of the present invention is that the process does not include biological reagents and substrates and that the product is free of impurifying biomaterials.

Starting material used in the present invention for producing highly purified menotropins and highly purified FSH is essentially obtained by a very well known method which employs kaolin to adsorb gonadotropins from the menopausal/postmenopausal urine (BP 1980). Briefly, bioactive fraction is extracted from the acidified urine with kaolin, eluted with alkali and precipitated with 2 volumes of acetone. Then, the bioactive fraction is extracted from this precipitate with 10% w/v solution of ammonium acetate in ethanol (70%) and precipitated with 10% ammonium acetate in ethanol (90%). Further purification is done by ion-exchange chromatography. The purified material obtained by this process constitutes the menotropins composition or some other equivalent preparation, like Fraction C.

Menotropins or equivalent (Fraction C) is chromatographed on a strong cationic exchange column, with the active fraction being eluted with a 0.2–0.5 M ammonium acetate buffer, pH 5.0–7.0. A new precipitate is obtained (Fraction F) by adding 4 volumes of ethanol. Fraction F is chromatographed on a strong anionic exchange column, with the active fraction being eluted with a 0.05–0.2 M ammonium acetate buffer, pH 5.0–7.0. The active fraction is frozen at −75° C. (Fraction G).

Fraction G is analyzed by a biological assay to determine precisely its FSH and LH content. Depending on the ratio found between both hormones, the following chromatographic step is taken, with two alternatives being possible:

1) co-purification of both hormones.

2) separation of the hormone activity which is in excess so as to obtain a Menotropins with 1:1 FSH/LH. Alternatively, separation of both FSH and LH provides both activities separately for therapeutic purposes (neat FSH and neat LH).

Once the steps to be taken are determined, Fraction G is dialyzed and concentrated so as to adapt it to the needs of the following chromatographic step. The resulting solution is chromatographed on a hydrophobic interaction column, eluting the active fractions according to two alternative processes taking into account options 1) and 2) above. The liquid fractions that are obtained (Fraction J2, J3, J4) are frozen at −75° C. Afterwards, these fractions are defrozen, dialyzed and concentrated, filtered through a sterilizing membrane and precipitated by adding 4 volumes of ethanol, obtaining a precipitate that is dried in vacuo to dryness (Fraction K).

BRIEF DESCRIPTION OF THE DRAWINGS

FIG. 1 represents an electrophoretic run of the conventional product (HMG) vs. the new highly purified menotropins product (Fraction KM).

FIG. 2 represents a PAGE (Polyacrylamide Gel Electrophoresis) run of highly purified Menotropins (Fraction $K_M$) run in different concentrations together with the molecular weight standards.

FIG. 3 represents a PAGE run of a highly purified FSH (Fraction $K_F$) in different concentrations together with the molecular weight standards.

FIG. 4 represents a PAGE run of: 1) Gonal-F (Serono) 1 FSH IU/μl, 2) Metrodine HP (Serono) 3 FSH IU/μl, 3) Highly Purified Menotropins (Fraction $K_M$) 3.7 FSH IU/μl and 4) Molecular Weight Standards (from the top) 14,400 D, 20,100 D, 30,000 D, 43,000 D, 67,000 D and 94,000 D.

FIG. 5 represents an Isoelectric focusing on 3–10 Phast-Gels silver stained, wherein: Lane 1 corresponds to the Calibration Kits for Broad 3–10 pI., Lane 2 corresponds to pI 4.55 standard (soybean trypsin inhibitor), Lane 3 corresponds to pI 5.85 standard (bovine carbonic anhydrase B), and Lanes 4, 5 and 6 correspond to highly purified follitropin ($K_F$) product (3 different production batches).

FIG. 6 represents an Isoelectric focusing on 3–10 Phast-Gels silver stained, wherein Lane 1 corresponds to the Calibration Kits for Broad 3–10 pI. and Lane 2 corresponds to highly purified menotropins ($K_M$) product.

FIG. 7 is the result obtained by HPLC with a Highly Purified Menotropins (Fraction $K_M$) sample.

FIG. 8 is the result obtained by HPLC with a Highly Purified FSH (Fraction $K_F$) sample.

FIG. 9 is the result obtained by HPLC with a sample of Gonal-F (Serono). (The peak at retention time 11.2 corresponds with an excipient of the pharmaceutical preparation), and FIG. 10 is a process Flow chart for obtaining the highly purified gonadotropins of the present invention.

DETAILED DESCRIPTION OF THE INVENTION a) Flow chart

The flow chart for obtaining highly purified gonadotropins is shown in FIG. 10.

The elaboration technique of Fraction $K_M$ constituting purified Menotropins will be described below.

b) Preparation of Fraction F

Fraction C is chromatographed on a chromatographic column containing 10 liters of strong cationic exchange resin of the sulphopropyl type.

Fraction C (110–140 g) is dissolved in 1600–1800 ml of a 0.05–015 M ammonium acetate solution, pH 5.0–7.0. The column is run and eluted with the necessary amount of 0.05–0.15 M ammonium acetate solution to bring the volume to 20 liters. The elution is continued with solutions of 0.15–0.20 M ammonium acetate, pH 5.0–7.0 (20 liters) and 0.2–0.5 M ammonium acetate, pH 5.0–7.0 (20 liters). The active fraction eluted with the latter solution is added with stirring to 4 volumes of 96% ethanol and enough acetic acid to reach a mixture pH of 5.5–5.7. A precipitate is formed, separated by centrifugation, washed with ethanol and dried in vacuo until ethanol is removed and humidity is lower than 5% (Fraction F).

c) Preparation of Fraction G

Fraction F is chromatographed on a chromatographic column containing 4 liters of strong anionic exchange resin of ammonium quaternary type Fraction F (40–60 g in 650 ml) is dissolved in 0.01–0.05 M ammonium acetate solution, pH 5.0–7.0, the column is run and eluted with the same solution to bring the volume to 7 liters. Elution is continued with 12 liters of 0.05–0.07 M ammonium acetate pH 5.0–7.0, then with 10 liters of 0.07–0.2 M ammonium acetate pH 5.0–7.0. The active fraction eluted with the latter solution is subjected to an ultrafiltration process using a PM 10 (10000 D) Ultrafilters (Amicon-Millipore) membrane. The solution is concentrated and dialyzed against 50 mM sodium phosphate buffer, pH 5.5–5.7 to a concentration of 2–4 g of protein in 100–150 ml of buffer. Then it is frozen at −75° C. (Fraction G).

d) Preparation of Fraction J

Fraction G is chromatographed on a chromatographic column containing 400 ml of a hydrophobic interaction resin (Phenyl Sepharose HP, Amersham-Pharmacia Biotech).

A sufficient amount of ammonium sulfate is added to the solution of Fraction G to obtain a 0.8–1.2 M concentration.

The chromatographic process to be carried out will allow the co-purification of FSH and LH or the separation of both hormones. The course of action will depend on the prior analyses conducted with Fraction G (biological assays), through which the FSH:LH ratio has been determined. Once this ratio is known, the overstock of the hormone in excess of 1:1 FSH:LH ratio will be removed.

d-1) If the product is balanced (1:1 FSH:LH), the chromatography of concentrated and dialyzed Fraction G will be conducted as follows:

Put the solution of Fraction G in the chromatographic column, 0.8–1.2 M in ammonium sulfate.

Elute with 2 volumes of 50–200 mM sodium phosphate buffer, 0.8–1.2 M ammonium sulfate, pH 5.0–7.0.

Continue the elution with 2 volumes of 50–200 mM phosphate buffer (50–70 % v/v) and 96% ethanol (50–30% v/v).

The active fraction eluted with the latter buffer (Fraction J4) is frozen at −75° C. This fraction has FSH and LH activity.

d-2) If the FSH:LH ratio of Fraction G is different from 1:1, the overstock of the hormone in excess will be removed as follows:

Run an aliquot of the solution of fraction G in the chromatographic column. 0.8–1.2 M in ammonium sulfate.

Elute with 2 volumes of 50–200 mM sodium phosphate buffer, 0.8–1.2 M ammonium sulfate. pH 5.0–7.0.

Continue the elution with 2 volumes of 50–200 mM sodium phosphate buffer, 0.4–0.6 M ammonium sulfate, pH 5.0–7.0, and finally with 2 volumes of 50–200 mM phosphate buffer (50–70% v/v) and 96% ethanol (50–30% v/v).

The active fraction eluted with 50–200 mM sodium phosphate buffer, 0.4–0.6 M ammonium sulfate (Fraction J2) is frozen at −75° C. This fraction has mostly FSH activity.

The active fraction eluted with 50–200 mM phosphate buffer (50–70% v/v) and 96% ethanol (50–30% v/v) (Fraction J3) is frozen at −75° C. This fraction only has LH activity.

Preparation of Fraction K

Fractions J2, J3, J4 are defrozen, dialyzed and concentrated using ultrafiltration through a PM 10 (Diaflo Ultrafilters, Amicon-Millipore) membrane against a 50 mM sodium phosphate buffer, pH 5.7.

Each resulting solution is filtered using a 0.45μ membrane under the necessary conditions to obtain a sterile product, and then added to 4 volumes of 96% ethanol and enough acetic acid to obtain a mixture pH of 5.5–5.7. The mixture is allowed to stand overnight. The precipitate is separated by centrifugation and dried in vacuo until ethanol is removed and humidity is lower than 5% (Fraction K).

Properties of Fraction K may vary depending on the precipitated fraction being J2, J3 or J4. Fraction $K_M$ obtained from Fraction J4 will contain approximately equivalent units of FSH and LH. Fraction $K_F$ obtained from Fraction J2 will be comprised of FSH and LH traces. Fraction $K_L$ obtained from Fraction J3 will be comprised of LH and FSH traces.

EXAMPLES OF BATCHES PRODUCED BY THE DESCRIBED TECHNIQUES

Example 1

1.1 Preparation of Fraction F 231.2 g of Fraction C were divided in two equal portions and chromatographed in two equivalent processes on a chromatographic column as above described.

115.6 g of Fraction C (in each process) were dissolved in 1700 ml of 0.05 M ammonium acetate buffer, pH 5.0 The column was run and eluted with further 18.7 liters of the same chromatographic buffer. The elution was continued with 20 liters of 0.15 M ammonium acetate buffer, pH 5.0 and finally with 20 liters of 0.5 M ammonium acetate buffer, pH 5.0 The active fraction obtained by eluting with 0.5 M ammonium acetate (22 liters) was added with stirring to a solution of 88 liters of 96% ethanol and 2400 ml of acetic acid. The pH of the mixture was 5.7. The precipitate obtained was left in the refrigerator (2–8° C.) overnight. The precipitate was centrifuged, washed with 96% ethanol and dried in vacuo for 17 h.

On each of the two equivalent processes, two Fractions F of 20.7 g and 19.5 g were obtained, respectively.

1.2 Preparation of Fraction G

The two fractions F obtained in the above step were brought together and chromatographed on column according to the described technique.

40.2 g of Fraction F were dissolved in 650 ml of 0.01 M ammonium acetate buffer, pH 5.0. The column was run with this solution and eluted with 6350 ml of the same dilution buffer. The elution was then continued with 12 liters of 0.05 M ammonium acetate, pH 5.0 and then with 10 liters of 0.2 M ammonium acetate, pH 5.0. The active fraction (4500 ml) eluted with the latter solution was subjected to an ultrafiltration process using a PM 10 (10000 D) Diaflo Ultrafilters (Amicon-Millipore) membrane. The solution is concentrated and dialyzed against 50 mM sodium phosphate, pH 5.7 for obtaining a concentration of 2–4 g of protein in 150 ml of buffer. Final solution (400 ml) was frozen at −75° C.

Fraction G was biologically tested in animals detecting a FSH potency of 42.000 IU/ml and LH potency of 33,780 IU/ml. With this result, it was considered necessary processing a portion of the solution (80 ml) of Fraction G under conditions for separating FSH and LH fractions J2 and J3 respectively). The rest (320 ml) was chromatographed under conditions so as not to separate both hormones (fraction J4). Aliquots of Fraction J3 and Fraction J4 where then mixed to obtain a final FSH:LH ratio of approximately 1:1 (fraction $K_M$).

1.3 Preparation of Fraction J i) Preparation of Fractions J2 (Highly Purified FSH) and J3 (Highly Purified LH):

Ammonium sulfate was added to an aliquot of fraction g (80 ml) until a concentration 1 M. This solution was run in Phenyl-Sepharose HP chromatographic column and was eluted with 2 volumes of buffer, 50 mM sodium phosphate, 1 M sulfate ammonium, pH 5.1. The elution was continued with 2 volumes of buffer, 50 mM sodium phosphate, 0.5 M ammonium sulfate, pH 5.1, and finally with 2 volumes of 50 mM sodium phosphate buffer (60% v/v) and 96% ethanol (40% v/v).

The FSH active fraction eluted with buffer, 50 mM sodium phosphate, 0.5 M ammonium sulfate, pH 5.1 (Fraction J2) was dialyzed and concentrated using PM 10 membrane ultrafiltration (Diaflo Ultrafilters, Amicon-Millipore), against a 50 mM sodium phosphate buffer, pH 5.7, and then was frozen at −75° C.

The LH active fraction eluted with 50 mM sodium phosphate buffer (60% v/v) and 96% ethanol (40% v/v) (Fraction J3) was dialyzed and concentrated using PM 10 membrane ultrafiltration (Diaflo Ultrafilters, Amicon-Millipore), against a 50 mM sodium phosphate buffer, pH 5.7, and then was frozen at −75° C.

ii) Preparation of Fraction J4 (Highly Purified Menotropins)

A second aliquot of Fraction G (320 ml) was defrozen and ammonium sulfate was added until a 1 M concentration was obtained. This solution was run in a Phenyl-Sepharose HP chromatographic column and was eluted with 2 volumes of buffer 50 mM sodium phosphate, 1 M ammonium sulfate, pH 5.1. The elution was continued with 2 volumes of phosphate 50 mM (60% v/v) and 96% ethanol (40% v/v). The eluted fraction with this buffer (Fraction J4) was frozen at −75° C.

1.4 Preparation of Fraction K

Fractions J3 (40 ml) and J4 (25 ml) were defrozen, filtered through 0.45µ membrane under necessary conditions for obtaining a sterile product (final volume 100 ml), and then admixed and stirred with 4 volumes of 96% ethanol (400 ml) and acetic acid necessary for reaching a pH 5.5 (1 ml).

Fraction J2 (40 ml) was defrozen, filtered through a 0.45µ membrane under necessary conditions for obtaining a sterile product (final volume 60 ml), and then admixed and stirred with 4 volumes of 96% ethanol (400 ml) and acetic acid necessary for reaching a pH 5.5 (0.5 ml).

Fractions were allowed to precipitate in the refrigerator overnight at 2–8° C. The next morning, the highly purified menotropins precipitate, obtained from Fraction J3 y J4 was separated by centrifugation and dried in vacuo until ethanol was removed and moisture was lower than 5% (Fraction $K_M$, 4.50 g).

The highly purified FSH precipitate obtained from the J2 fraction was separated by centrifugation and dried in vacuo until ethanol was removed and humidity was lower than 5% (Fraction $K_F$, 0.55 g).

1.5 Results

The biological analysis performed with Fractions $K_M$ (highly purified menotropins) and $K_F$ (highly purified FSH) exhibited the following results:

| Fraction | FSH Potency (IU/mg) | Specific Activity (IU/protein mg) | LH Potency (IU/mg) |
| --- | --- | --- | --- |
| $K_M$ | 2,870 | 3,700 | 2,635 |
| $K_F$ | 6,895 | 8,900 | <1 LH IU/75 FSH IU |

Yield Table

| Fraction | FSH IU | LH IU | Yield relative Prior stage | | Total Yield | |
| --- | --- | --- | --- | --- | --- | --- |
| | | | FSH % | LH % | FSH % | LH % |
| C | 19,276,000 | 15,604,000 | — | — | — | — |
| F | 18,408,000 | 14,980,000 | 95.5 | 96.0 | 95.5 | 96.0 |
| G | 16,800,000 | 13,512,000 | 91.3 | 90.2 | 87.2 | 86.6 |
| $K_M$ | 12,915,000 | 11,857,000 | 76.9 | 87.8 | 67.0 | 76.0 |
| $K_F$ | 3,792,000 | 50,600 | 22.6 | — | 19.7 | — |

Example 2

2.1 Preparation of Fraction F 250.06 g of Fraction C were divided in two equal portions and chromatographed in two equivalent processes in a chromatographic column as the one described above.

125.03 g of Fraction C (in each process) were dissolved in 1,700 ml of 0.05 M ammonium acetate buffer, pH 5.1. Then, the column was run and eluted with further 18.7 liters of the same chromatographic buffer. The elation was continued with 20 liters 0.15 M ammonium acetate buffer, pH 5.1, and finally with 20 liters of 0.5 M ammonium acetate buffer, pH 5.1. The active fraction obtained by elution with 0.5 M ammonium acetate (22 liters) was added under stirring to 88 liters of 96% ethanol and 2,200 ml of acetic acid. The mixture pH was 5.7. It was observed the appearance of a precipitate. The mixture was left in the refrigerator at 2–8° C. overnight. The precipitated was centrifuged, washed with 96% ethanol and dried in vacuo for 22 hs.

In each of the equivalent processes, two fractions F of 21.57 g and 21.15 g were respectively obtained.

2.2 Preparation of Fraction G

The two fractions obtained in the previous stage were brought together and chromatographed on column according to the process described above.

42.58 g of Fraction F were dissolved in 650 ml of 0.01 M ammonium acetate buffer, pH 5.1. This solution was run in the column and eluted with 6.350 ml of the same buffer dissolution. The elution was continued with 12 liters of ammonium acetate 0.05 M, pH 5.0, and then with 10 liters of ammonium acetate 0.2 M, pH 5. The active fraction (4,500 ml) eluted with this last solution was subjected to an ultrafiltration process with a PM 10 membrane (10,000 D) (Diaflo Ultrafilters, Amicon-Millipore). The solution was concentrated and dialyzed against a 50 mM sodium phosphate buffer, pH 5.7, until a concentration of 2–4 g of protein in 150 ml of buffer is obtained. The final volume of 500 ml was frozen at –75° C.

Fraction G was biologically tested in animals, showing a FSH potency of 49,790 IU/ml and a LH potency of 39,600 IU/ml. With this analysis, it was considered necessary processing one part of the solution (100 ml) of Fraction G under conditions for separating FSH and LH (fractions J2 and J3 respectively) and the rest (400 ml) under conditions so as not to separate both hormones (J4).

Aliquots of Fraction J3 and Fraction J4 where then mixed to obtain a final FSH:LH ratio of approximately 1:1 (Fraction $K_M$).

2.3 Preparation of Fraction J i) Preparation of Fraction J2 (Highly Purified FSH) and J3 (Highly Purified LH):

Ammonium sulfate was added to one aliquot of Fraction G (100 ml) until a 1 M concentration is obtained. This solution was run in the Phenyl-Sepharose HP chromatographic column and was eluted with 2 volumes of buffer 50 mM sodium phosphate, 1 M ammonium sulfate, pH 5.1. Then the elution is continued with 2 volumes of buffer 50 mM sodium phosphate, 0.5 M ammonium sulfate, pH 5.1, and finally with 2 volumes of 50 mM sodium phosphate (60% v/v) and 96% ethanol (40% v/v).

The FSH eluted active fraction with buffer 50 mM sodium phosphate. 0.5 M ammonium sulfate, pH 5.1 (Fraction J2) was dialyzed, concentrated using membrane ultrafiltration with PM 10 membrane (Diaflo Ultrafilters Amicon-Millipore), against a 50 mM sodium phosphate buffer, pH 5.7, and then was frozen at –75° C.

The LH eluted active fraction with 50 mM sodium phosphate buffer (60% v/v) and 96% ethanol (40% v/v) (Fraction J3) was dialyzed, concentrated using membrane ultrafiltration with a PM 10 membrane (Diaflo Ultrafilters, Amicon-Millipore), against a 50 mM sodium phosphate buffer, pH 5.7, and then was frozen at –75° C.

ii) Preparation of Fraction J4 (Highly Purified Menotropins):

To a second aliquot of Fraction G (400 ml) ammonium sulfate was added until a 1 M concentration was obtained. The solution was run in Phenyl-Sepharose HP chromatographic column and was eluted with 2 volumes of buffer 50 mM sodium phosphate, 1 M ammonium sulfate, pH 5.1. The elution was continued with 2 further volumes of 50 mM phosphate buffer (60% v/v) and 96% ethanol (40% v/v). The active fraction eluted with this buffer (Fraction J4) was frozen at –75° C.

2.4 Preparation of Fraction K

Fractions J3 (50 ml) and J4 (30 ml) were defrozen, filtered through a 0.45% membrane under necessary conditions for obtaining a sterile product (final volume 110 ml), and then were added under stirring to 4 volumes of 96% ethanol (440 ml) and enough acetic acid to achieve a pH 5.5 (1 ml).

Fraction J2 (50 ml) was defrozen, filtered through a 0.45µ membrane under necessary conditions for obtaining a sterile product (final volume 70 ml), and then was added under stirring to 4 volumes of 96% ethanol (280 ml) and enough acetic acid to achieve a pH 5.5 (0.5 ml).

Fractions were allowed to precipitate in the refrigerator overnight at 2–8° C. The next morning, the highly purified menotropins precipitate, obtained from Fractions J3 and J4 was separated by centrifugation and dried in vacuo until ethanol was removed and moisture was lower than 5% (Fraction $K_M$, 5.71 g).

The highly purified FSH precipitate, obtained from Fraction J2, was separated by centrifugation, dried in vacuo until ethanol was removed and moisture was lower than 5% (Fraction $K_F$, 0.70 g).

2.5 Results

The biological analysis performed with Fractions $K_M$ (highly purified menotropins) and $K_F$ (highly purified FSH) showed the following results:

| Fraction | FSH Potency (IU/mg) | Specific Activity (IU/protein mg) | LH Potency (IU/mg) |
|---|---|---|---|
| $K_M$ | 3,344 | 4,300 | 3,022 |
| $K_F$ | 6,500 | 8,400 | <1 LH IU/75 FSH IU |

2.6 Yield Table

| Fraction | FSH IU | LH IU | Yield relative prior stage FSH % | LH % | Total Yield FSH % | LH % |
|---|---|---|---|---|---|---|
| C | 29,000,000 | 21,900,000 | — | — | — | — |
| F | 27,800,000 | 21,200,000 | 95.9 | 96.8 | 95.9 | 97.0 |
| G | 24,900,000 | 19,800,000 | 89.6 | 93.4 | 85.9 | 90.4 |
| $K_M$ | 19,094,000 | 17,255,000 | 76.7 | 87.1 | 65.8 | 78.8 |
| $K_F$ | 4,550,000 | <60,600 | 18.3 | — | 15.7 | — |

High purified products were also obtained using the process of the present invention starting with less active materials. In this case an FSH of about 5000 IU/mg protein and menotropins of a potency of about 2500 IU/mg protein for both FSH and LH were obtained.

2.7 Characterization of the Obtained Products

Fractions $K_{A1}$ and $K_F$ were characterized by the following techniques:

2.7.a) Polyacrylamide gel Electrophoresis (PAGE)
2.7.b) Polyacrylamide gel Electrophoresis followed by Western-blot analysis
2.7.c) Isoeiectrofocusing
2.7.d) Size exclusion chromatography (SEC) in HPLC
2.7.e) Protein contents measurement
2.7.f) Biological potency dosage in animals (previously informed)

2.7.a) Polyacrylamide gel Electrophoresis (PAGE)

Fractions $K_M$ and $K_F$ were analyzed by electrophoresis according to the following procedure:

Equipment: Ultrathin Polyacrylamide Gel Electrophoresis System, PhastSystem (Amersham Pharmacia Biotech).
Gels: Phast Gel gradient 8–25 (Amersham Pharmacia Biotech).
Buffer: Buffer strips/SDS (Amersham Pharmacia Biotech).
Separation Technique: File 110, PhastSystem, SDS-Page
Development Technique: File 200, PhastSystem for Coomasie Brilliant Blue.
Low Molecular Weight Probes: Electrophoretic Calibration Kit containing 6 purified proteins (Amersham Pharmacia Biotech).

| | Molecular Weight |
|---|---|
| Phosphorylase b | 94,000 D |
| Albumin | 67,000 D |
| Ovoalbumin | 43,000 D |
| Carbonic Anhydrase | 30,000 D |
| Trypsine inhibitor | 20,100 D |
| α-lactalbumin | 14,400 D |

Each kit vial contains a lyophilized blend with approximately 100 μg of each protein. Each vial was dissolved with 100 μL of sample buffer.

Sample Buffer:

250 mg of SDS and 0.5 ml of β-mercaptoethanol were dissolved in 10 ml of buffer A.

| Buffer A: | EDTA 1 mM | 372 mg |
|---|---|---|
| | TRIS 10 mM | 1.21 mg |
| | H20 q. s. t. | 1,000 ml |
| | pH 8.0 | |

The samples were dissolved so that the final concentration was 1,100–1.300 FSH IU/ml of sample buffer.

Sample treatment

The sample was heated at 100° C. for 5 minutes. Blue bromophenol was added until a 0.01% concentration was obtained.

After the Electrophoretic run and the development, the gels were dried with hot air.

Obtained Results

The electrophoresis runs of Fractions $K_M$ (FIG. 2) and $K_F$ (FIG. 3) gave as result a profile in which it is observed in an almost exclusively way a unique band developed with Brilliant Coomassie Blue with a migration distance midway of the standards of molecular weight 20,100 D and 30,000 D, indicating an approximate molecular weight of 25,000 D.

| Sample | Rf |
|---|---|
| Std. 20,100 D | 0.196 |
| Fractions $K_M$–$K_F$ | 0.250 |
| Std. 30,000 | 0.300 |

The assignment of the observed band in the electrophoresis of Fractions $K_F$ and $K_M$ was performed by two ways:

a) by comparison with 2 commercial products containing FSH as the sole active ingredient: Gonal-F (Serono) containing FSH of recombinant origin, Metrodine HP (Serono) containing FSH of urinary origin (see FIG. 4).

b) by Electrophoresis-Western blot as was indicated in 2.7.b).

2.7.b) Polyacrylamide Gel Electrophoresis followed by Western-Blot analysis.

The samples of fractions $K_M$ and $K_F$ were analyzed by Western blot. After performing a polyacrylamide electrophoresis process in gradient similar to the one described in 2.7.a), the bands were transferred to a nitrocelluose support and developed by antibody action. Specific antibodies for chain β-FSH, chain β-LH and against chain α of both hormones were used.

Technique: The transfer technique No. 221 was used for the PhastSystem (Amersham Pharmacia Biotech), employing the following transfer buffer:

Transference buffer: Tris 25 mM, Glycine 192 mM, pH 8.3, containing, 20% methanol.

Membrane: Probind 45, 0.45 μm pore

Transfer conditions: 25 V, 25 mA, 1 W, 45 min.

Stained with Coomassie Blue:

Staining Solution: 0.1% solution of Phast Gel Blue R in methanol 30% and acetic acid 10% in distilled water.

Final Solution: Mix 1 part of the staining solution with 1 part of acetic acid 20% in distilled water.

Procedure: Color the membrane in the final solution for 30 minutes with gentle stirring. Wash the membrane with solution of methanol:water:acetic acid (30:60:10) twice and then with acetic 20%.

Procedure of detection: The detection method by streptavidine-biotine was used.

Buffer used: PBS (sodium phosphate 0.01 M, sodium chloride 0.25 M, pH 7.6).

Blocking solution: Albumin 5% in PBS.

Washing solution: a) Albumin 5% in PBS, b) PBS.

Primary antibody solution: The following primary antibodies were used.

1) anti β-LH monoclonal antibody (Immunotech) (IgG1-mice), Catalogue No. 0374.

2) anti β-FSH monoclonal antibody (Immunotech) (IgG1-mice), Catalogue No. 0373.

3) monoclonal antibody against α-subunit of pituitary hormones (Immunotech) (IgG1-mice), Catalogue No. 0375.

Dilution: dilute the primary antibody 1:100.

Secondary antibody solution: The secondary antibody used was: Biotin-SP-conjugated AffiniPure F(ab')$_2$ Fragment Goat Anti-Mouse IgG (H+ L), (heavy chain and light chain). (Immunotech, Cat. No. 0816) diluted 1:500 in PBS.

Peroxidase-conjugated Streptavidine solution: A dilution 1:500 in PBS of Peroxidase-conjugated Streptavidine (Immunotech, Cat. No. 0309) was used.

Development solution: Horseradish Peroxidase conjugate substrate kit (Bio Rad, Cat No. 170-6431), containing a solution blend of oxygenated water, 4-chloro-1-naphtol and buffer for developing the color, was used for preparing 1 liter of solution.

Brief Description of the Procedure:

1) incubate the membrane with blocking solution overnight.

2) wash with washing solution a) twice for 5 min. each time.

3) incubate with primary antibody solution overnight.

4) wash with washing solution a) three times for 5 minutes each time.

5) incubate with secondary antibody for 1 hour.

6) wash with washing solution a) three times for 5 minutes each time.

7) incubate with conjugated peroxidase for 30 minutes.

8) wash with washing solution a) three times for 5 minutes each time.

9) incubate with developing solution for 10 minutes.

10) stop the reaction.

Results

After performing the polyacrylamide gel electrophoresis of Fractions $K_M$ and $K_F$, the bands were transferred to nitrocellulose membranes according to the above informed technique, and developed. The following results were found.

| Fraction | Anti-β FSH antibody | Anti-β LH antibody | Anti-α-LH antibody |
|---|---|---|---|
| $K_M$ | Positive | Positive | Positive |
| $K_F$ | Positive | Negative | Positive |

In view of these results, it is concluded that the band developed with Coomassie Blue in the electrophoresis of fraction $K_M$ had both FSH and LH activities. Instead, fraction $K^F$ only reacted positively against the specific antibody for FSH, and not for LH. Given that α-chain of FSH and LH are common, both fractions KM and KF showed a positive reaction with an antibody against the α-chain.

2.7.c) Isoelectrofocusing

Fractions $K_M$ (highly purified FSH) and $K_F$ (highly purified FSH) were analyzed by isoelectrofocusing according to the following procedure:

Equipment: Ultrathin Polyacrylamide Gel Electrophoresis System, PhastSystem (Amersham Pharmacia Biotech).

Gels: Phast Gel IEF 3–9 (Amersham Pharmacia Biotech).

Separation Technique: File 100, PhastSystem.

Development Technique: Silver Kit (Amersham Pharmacia Biotech).

PI Standards: IEF calibration kit; Broad pI Kit 3–10) (Amersham Pharmacia Biotech). Soybean trypsin inhibitor, pI 5.85(Sigma). Bovine carbonic anhydrase, pI 4.55 (Sigma).

Sample Treatment

Samples were dissolve to have a concentration of 2.5 mg/ml to 1.25 mg/ml.

After the electrophoretic run and the development, the gels were dried with hot air.

Obtained Results

The pI distribution for both the $K_F$ (highly purified FSH) and $K_M$ (highly purified menotropins) are shown in FIG. 5 and FIG. 6. The acidic nature of the gonadotropins is confirm by the IEF pattern. In fact, as fully described in the literature, isoforms are restricted to the acidic range.

2.7.d) Size exclusion Chromatography (SEC) in HPLC

Description of the equipment:

High performance liquid chromatograph Shimadzu, LC-10AVP, with manual injector 7725i, with position sensor and loop of 20, 50 or 200 μL, Rheodyne.

UV-visible Spectrophotometer detector., model SPD-10AVP, Shimadzu (190–600 nm).

Working station for processing chromatographic data Shimadzu Class-CR 10, program Class CR10 and module CBM-101.

Chromatographic column Bio-Rad BIO-SIL™ SEC250 silica-based size exclusion column (300×7.5 mm)

Flow: 1.0 ml/min.

Detection: UV at 220 nm.

Column Temperature: room temperature

Injection volume: 50 to 200 μL.

Sample preparation: Inject approximately 1 ml of the mobile phase in the vial containing the sample, stir until dissolution.

Results:

The following chromatograms of Fractions $K_M$ and $K_F$ showed the presence of only one peak at a retention time of approximately 8.1–8.2 sec. The retention time coincides with the one obtained by chromatography of a commercial product, Gonal-F (Serono) containing recombinant FSH. (See FIGS. 7, 8 and 9)

2.7.e) Protein Dosage:

Method: The method of Lowry [Journal of Biological Chemistry 193, 265 (1951)] with a Folin-Ciocalteu reactive, and a standard curve of albumin.

Results: The protein percentage for both fractions $K_M$ and $K_F$ indicated in examples 1 and 2 was approximately 77%.

2.7.f) Biological Potency Dosage in Animals.

As it was previously reported in section 2.5, fractions $K_M$ and $K_F$ were biologically analyzed in rats.

Methods:

2.7.f.1) FSH Biological Potency Dosage

The Steelman-Pohley method [Steelman, S. L. & Pohley, F. M., Endocrinology 53, 604 (1953)] of ovarian weight increase was used in immature 21–24 days-old female rats, injected with three doses of a product containing FSH. The doses should keep a ratio such that the difference between the logarithms of the greater dose and the medium dose is equal to the difference between the logarithms of the medium dose and the smaller dose. Animal lots were used in which the weight difference between the heaviest and the lightest animal was not more than 10 grams. The animals were injected subcutaneously during three days with three different doses of the sample dissolved in phosphate/albumin buffer and the corresponding doses of a standard. On the fifth day the animals were sacrificed, the ovaries were extracted and weighted. The data obtained with sample were compared with the data obtained with the standard and the potency of the different samples was calculated using the statistical scheme indicated for the analysis of a sample against standard in a 3×3 test (see Biological Analysis of USP XXIII).

2.7.f.2) LH Biological Potency Dosage

The method of weight increase of seminal vesicle in immature 21–24 days-old male rats injected with three doses of a product containing LH was used. The three doses should keep a ratio such that the difference between the logarithms of the greater dose and the medium dose is equal to the difference between the logarithms of the medium dose and the smaller dose. Animal lots were used in which the weight difference between the heaviest and the lightest animal was not more than 10 grams. The animals were injected subcutaneously during four days with three different doses of the sample dissolved in phosphate/albumin buffer and the corresponding doses of a standard. On the fifth day the animals were sacrificed, the seminal vesicles were extracted and weighted. The data obtained with sample were compared with the data obtained with the standard and the potency of the different samples was calculated using the statistical scheme indicated for the analysis of a sample against standard in a 3×3 test (see Biological Analysis of USP XXIII).

The standard used was a sample of Menotropins calibrated against the 3rd international standard of urinary FSH and LH prepared by the NIBSC (National Institute of Biological Standards and Control—Great Britain) depending on the WHO (World Health Organization).

Example 3

Pharmaceutical Preparations

Highly purified injectable menotropins specialty:

Excipients that may be used in the composition are lactose, mannitol, and mixtures thereof. Other conventional excipients can also be used.

In the present invention, lactose was used as an excipient in the injectable preparation.

The preparation pH can be corrected to a value in the range of 6,0–7,0 by adding acids or bases (phosphoric acid or others and/or sodium phosphate or others).

3 ml borosilicate glass type I vials with bromobutyl stoppers are used as containers.

Preparation of a Batch of 5,000 Ampoules

The calculated amount of menotropins of high purity (with a 10% overfilling) is dissolved in 500 ml of water for injection. On the other hand, 100 gr. of lactose is dissolved in 4 liters of water for injection. Both solutions are mixed, the pH is adjusted, if necessary, by the addition of an acid or base, the resulting solution is completed to 5,000 ml and sterilized by filtration through a of 0.2μ membrane. Vials are filled with the prepared solution (1 ml) and loaded into a sterile lyophilizer at a temperature of –40° C. for at least 8 hr. The lyophilization starts heating at 3° C./hr up to temperature of +30° C., which is maintained till the end of the cycle.

The present example is similarly applied for the preparation of highly purified follitropin.

We claim:

1. A purification process for obtaining the human urinary gonadotropins follicle-stimulating hormone (FSH) and/or luteinizing hormone (LH) of high biological activity and chemical purity absolutely free of foreign contaminating materials derived from the use of biological reagents or chromatography dyes, from crude gonadotropins comprising FSH LH, said process comprising the following steps:
   1) purifying said gonadotropins diluted in 0.05–0.15 M ammonium acetate, pH5.0–6.0, in an ionic exchange column with a strong cationic sulfopropyl resin, eluting both FSH and LH with solutions of 0.05–0.5 M ammonium acetate, pH 5.0–7.0; and
   2) purifying the gonadotropins diluted in 0.01–0.05 M ammonium acetate, pH 5.0–7.0, in an ion exchange column with a strong anionic resin of the quaternary ammonium type, eluting both FSH and LH with solutions of 0.05–0.2 M ammonium acetate, pH 5.0–7.0; and
   3) purifying the gonadotropins in a column with an hydrophobic interaction resin by sequential addition of at least two of the following solutions:
      a) buffer of 50–200 mM sodium phosphate, and 0.8–1.2 M ammonium sulfate, pH 5.0–6.0;
      b) buffer of 50–200 mM sodium phosphate, and 0.4–0.6 M ammonium sulfate; pH 5.0–7.0;
      c) buffer of 50–200 mM sodium phosphate (50–70% v/v), and ethanol 96% (50–30% v/v), and
   4) recovering purified FSH and/or LH;
   wherein steps 1 to 3 may be performed in any order.

2. The purification process of claim 1 wherein the strong cationic resin in step 1) is a SP-Sepharose resin.

3. The purification process of claim 1 wherein the strong anionic resin in step 2) is a Q-Sepharose resin.

4. The purification process of claim 1 wherein the hydrophobic interaction resin in step 3) is a Phenyl-Sepharose resin.

5. The purification process of claim 1, wherein the FSH is eluted with solution b, and the LH is eluted with solution c, in the addition sequence a, b, c in step 8.

6. The purification process of claim 1, wherein if the ratio of FSH: LH is approximately 1:1, the gonadotropins are eluted with solution c, in an orderly addition sequence a, c in step 3.

7. The purification process of claim 1, wherein if the ratio of FSH: LH is different from 1:1, the process further comprises the addition of gonadotropin FSH eluted with solution b, or the addition of gonadotropin LH eluted with solution c, in an orderly addition sequence a, b, c in step 3.

8. The purification process of claim 1, wherein said crude gonadotropins are obtained from urine of menopausal and/or post-menopausal women.

9. The purification process of claim 1, wherein said crude gonadotropins have FSH activity greater than 40 IU/mg and LH activity greater than 40 IU/mg.

* * * * *